United States Patent [19]

Blum

[11] Patent Number: 4,584,996

[45] Date of Patent: Apr. 29, 1986

[54] APPARATUS FOR CONSERVATIVE SUPPLEMENTAL OXYGEN THERAPY

[76] Inventor: Alvin S. Blum, 2350 Del Mar Pl., Fort Lauderdale, Fla. 33301

[21] Appl. No.: 588,691

[22] Filed: Mar. 12, 1984

[51] Int. Cl.$^4$ ............................................ A61M 16/00
[52] U.S. Cl. ............................ 128/204.21; 128/207.18
[58] Field of Search ....................... 128/204.21, 204.22, 128/204.23, 204.24, 204.26, 205.13, 205.17, 205.25, 207.18

[56] References Cited

U.S. PATENT DOCUMENTS 4,163,450  8/1979  Kirk et al. ......................... 128/204.23
4,484,578  11/1984  Durkan ............................ 128/207.18

Primary Examiner—Henry J. Recla
Attorney, Agent, or Firm—Alvin S. Blum

[57] ABSTRACT

Method and apparatus for intermittent administration of supplemental oxygen to patients with chronic obstructive lung disease. The apparatus is programmable for the specific oxygen requirements of the patient and is responsive to changes in requirements with increased patient activity. Patient's arterial blood oxygen level is measured while supplying oxygen to determine the number of respiratory cycles required to reach a first desired arterial blood oxygen level and it is again measured without supplemental oxygen to determine the number of respiratory cycles required to diminish to a second, lower particular level. These two cycle numbers are applied as a program to apparatus having respiratory cycle sensing and counting and control valve means to provide a regulated flow of supplemental oxygen to a nasal cannula for a predetermined number of on respiratory cycles and to shut off the flow for a preset number of off respiratory cycles sequentially and repetitively. The oxygen conservation properties are further enhanced by turning off the oxygen flow during the exhalation phase of each respiratory cycle throughout the on respiratory cycles. As the respiratory rate increases with activity, the duration of the on and off periods thereby changes accordingly. Performance may be further enhanced by means changing the programmed cycle numbers and ON/OFF intervals in response to changes in the respiratory rate.

20 Claims, 2 Drawing Figures

APPARATUS FOR CONSERVATIVE SUPPLEMENTAL OXYGEN THERAPY

BACKGROUND OF THE INVENTION

This invention relates to systems for supplying supplemental oxygen to a patient intermittently with the supply on for a predetermined number of ON respiratory cycles and the supply off for a predetermined number of OFF respiratory cycles. Oxygen saving is further enhanced by shutting the oxygen flow off during the exhalation phase of each ON respiratory cycle.

The incidence of chronic obstructive lung disease (C.O.L.D.) is increasing. These patients have inadequate pulmonary gas exchange resulting in inadequate oxygenation of blood passing through the lungs. Inadequate blood oxygenation and consequent body tissue hypoxia account for the disabling effects of the disease. It has been demonstrated that continuous administration of supplemental oxygen by nasal cannula overcomes the functional disability and greatly improves the quality of life as well as prolonging life. It is now common practice for ambulatory patients to carry an oxygen supply weighing nine pounds and lasting 3–4 hours. Prior art devices conserve oxygen by shutting off the gas flow during the exhalation phase of each respiratory cycle, which may double the effective supply.

BRIEF SUMMARY OF THE INVENTION

Restricted mobility, activity and costs of C.O.L.D. therapy may be effectively reduced by intermittent oxygen therapy. This intermittent oxygen therapy can replace continuous oxygen therapy because of the unusual physiological nature of C.O.L.D.. To conserve oxygen, a number of oxygen supply systems turn off the oxygen flow during exhalation and turn on the oxygen flow only during inhalation. It is an object of this invention to further extend and conserve the oxygen supply by turning the oxygen flow off for a predetermined number of OFF respiratory cycles, and then turning the flow on only during inspirations for a predetermined number of ON cycles. When physical exertion increases oxygen requirements, the respiration rate will also increase, thereby shortening the ON/OFF time intervals correspondingly. Alternatively performance may be further enhanced by programmatically changing cycle numbers, flow rates, and ON/OFF intervals in response to respiratory rate.

C.O.L.D. destroys lung tissue and impairs the lung's blood supply. As a consequence, the gas exchange behavior of the lungs is impaired, resulting in diminished oxygenation of the arterial blood. When such patients breathe air enriched with supplemental oxygen, the partial pressure of oxygen within the lungs is increased. This improves the transfer of oxygen from the lung to the blood and increases the oxygen content of the blood.

When oxygen administration is discontinued and the patient is returned to breathing room air, the arterial oxygen content remains elevated for a varying period. The oxygen content only very slowly returns to that value obtained while breathing room air. Depending upon the degree of pulmonary abnormalities, this may require 20-25 minutes. By contrast, patients with previously normal lungs requiring oxygen therapy (example: patients with heart failure), will promptly return to the value obtained while breathing room air (3-5 minutes).

Since many C.O.L.D. patients maintain an adequate level of arterial blood oxygenation for a prolonged period following cessation of oxygen administration, advantage is taken of this response by discontinuing oxygen therapy while the oxygen level still remains at an appropriate value. Discontinuation during this time conserves oxygen. When the arterial oxygen saturation has decayed to a predetermined lower value, oxygen administration is restarted, and continues until appropriate oxygenation of the blood is reestablished. At this time administration is again discontinued. These cycles repeat on a continuous basis administering $O_2$ intermittently to maintain adequate arterial oxygenation.

C.O.L.D. patients have many abnormally enlarged spaces within their lungs that are slowly ventilated and have a very poor blood supply. These areas act as "internal reservoirs" which store air enriched with oxygen when such is being breathed. When regular air breathing is resumed, these areas transfer the oxygen enriched air to adjacent areas of the lungs with a better blood supply and act as a source of continued oxygenation of the blood for some time after supplemental oxygen has been discontinued.

Recently developed sophisticated instrumentation (Hewett-Packard Ear Oximeter, Model 47201A) allows for the continuous determination of arterial oxygen saturation—an index of oxygen content. This is a painless, non-invasive method. Determination of the time to obtain appropriate oxygenation at a selected flow of oxygen (usually 2L/Min) establishes the "on" time of oxygen administration. After this value is determined, a recording is made of the rate of decline in the oxygen saturation after oxygen has been discontinued. This defines the "off" time.

The respiratory rate in cycles per minute is determined. The "on" time and the "off" time in minutes are multiplied by respiratory rate in cycles per minute to get ON cycle number and OFF cycle number. These are the number of respiratory cycles that the gas flow can be ON and OFF in sequence while maintaining the arterial blood oxygen concentration within the two desired levels at the selected flow rate. These three values, ON number, OFF number and flow rate are entered into the oxygen delivery system of the invention. The unit is connected between the oxygen supply source and the patient. Oxygen is generally conveyed from the apparatus to the patient by plastic tubing terminating in the nasal prongs. Thusly, the system continuously and automatically delivers oxygen intermittently to the subject as required. By shutting off gas flow completely during the OFF cycles the system conserves at least 50% of the oxygen when compared to prior art continuous systems. And by shutting off during the expiratory phase of the ON cycles, the system further conserves at least 50% of the remaining supply so that the overall savings of gas may be more than 75% when compared to prior art continuous systems.

It is an object of the invention to provide a method for intermittent oxygen therapy for a C.O.L.D. patient which is supplemental to the patient's normal room air intake. This is generally delivered via a loosely fitting nasal cannula without altering the pressure relationships within the respiratory tract. When the patient inhales while gas is supplied to the cannula, the volume of gas inhaled is not changed, only the concentration of oxygen is increased. This is in contrast to respirators and ventilators which form a closed circuit with the respiratory tract and provide alternate pressure and suction to move all gas into and out of the lungs at different phases of each respiratory cycle. It is an object of this invention to provide a system which periodically administers supplemental oxygen during an ON interval measured over a predetermined number of respiratory cycles followed by an OFF period extending over a predetermined number of respiratory cycles, wherein the ON and OFF cycle numbers are independently adjustable and are predetermined from prior measurements of the patient's requirements for such therapy. These and other features, objects and advantages will become more apparent from the following description and drawing of preferred embodiments of the invention wherein:

The specific apparatus illustrated utilizes the operative principles or features of the invention set forth and defined in the appended claims. It is considered reasonably self-evident that these principles or features can be utilized within a wide variety of differently constructed and/or differently appearing oxygen dispensing apparatuses through the use of exercise of routine skill in the art without departing from the essential characteristics of the invention.

DESCRIPTION OF PREFERRED EMBODIMENTS

Figure 1:
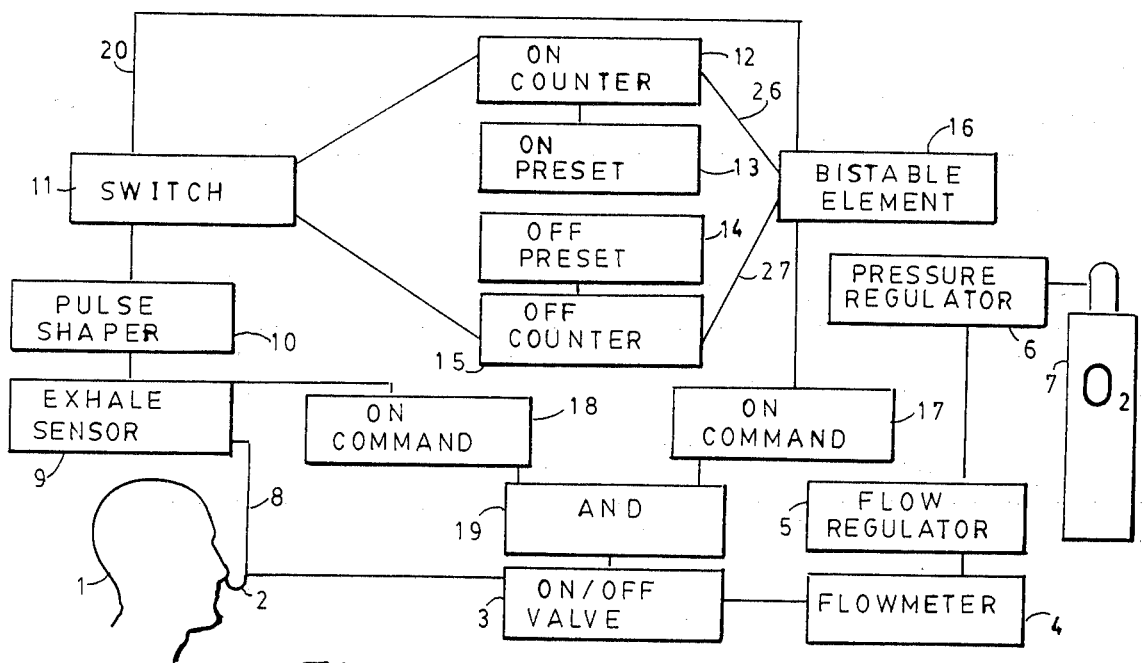
FIG. 1 is a schematic view of a dispensing system for the intermittent administration of oxygen through a cannula to a patient which features the oxygen conserving functions of the invention for shutting off the flow of oxygen during those periods when it is not useful.

Referring now to FIG. 1, the patient 1 receives a flow of oxygen through a nasal cannula 2 connected to a portable or stationary supply of oxygen 7 which may be a compressed gas cylinder, a liquified gas container, an oxygen concentrator, a piped-in wall outlet or the like. The supply will generally be controlled by a pressure regulator 6, a flow controller 5, a flow meter 4 and an on/off valve 3. Exhale sensor 9 is connected to the patient by sensor connection 8. As illustrated, this may be a gas tube either directly connected to the nasal cannula or to the tubing connected to the nasal cannula. The pressure in sensor connection 8 will change with the respiratory cycle, being lower during the inhale phase and higher during the exhale phase. Exhale sensor 9 converts the gas pressure into an electrical signal, sending out a positive electrical signal to a first command element 18 and also to pulse shaper 10 whenever the gas pressure in connection 8 is not high, i.e. a positive signal output occurs whenever subject is not exhaling. Pulse shaper 10 puts out a single output pulse every time it receives a positive going output signal from exhale sensor 9. The pulse from pulse shaper 10 passes through two-position switch 11 to either ON counter 12 or OFF counter 15. The position of switch 11 is controlled by bistable element 16 through switch control line 20. In a first condition of bistable element 16, it sends a positive output through control line 20 to maintain switch 11 in a first position, wherein pulses from pulse shaper 10 are fed to ON counter 12 which adds up the incoming pulses. At the same time, the positive output of bistable element 16 is also sent to the second ON command element 17. Logic AND element 19 responds to positive signals on both command inputs 17 and 18 by turning on the on/off valve 3. Command element 17 will be sending out a positive signal continuously throughout all the ON respiratory cycles and command element 18 will only send out a signal when the patient is not exhaling. This results in the ON/OFF valve 3 being off during exhale and on during inhale while the ON counter 12 is counting. Preset element 13 has been set to the desired number of ON cycles as determined by prior blood gas measurements. Preset element 13 controls ON counter 12, stopping the count when the preset number of cycles has been reached, and signalling through first input 26 to bistable element 16 to switch it from its first condition to its second condition. In the second condition of bistable element 16 there is a negative signal to ON command 17 and to switch 11 causing switch 11 to assume a second position in which pulses from pulse shaper 10 are now fed to OFF counter 15. And ON/OFF valve 3 remains OFF. Preset element 14 has been set to the desired number of OFF cycles as determined by prior blood gas measurements. Preset element 14 controls OFF counter 15, stopping the count when the preset number of cycles has been reached, and signalling through second input 27 to bistable element 16 to switch it from its second condition to its first condition. The ON counting cycle now begins again and the cycles continuously repeat according to the preset program.

The ON/OFF requirements are generally determined by blood gas measurements made when the patient is at rest. When the patient is active, his oxygen requirements will increase. The rate of respiration will rise and the rate of rise and fall of blood oxygen with and without supplemental oxygen can also be expected to increase. Since the ON/OFF periods are based on number of respiratory cycles and not time, the increased respiratory rate will automatically cause the ON/OFF periods to be shorter, which should properly accommodate to the new requirements.

Figure 2:
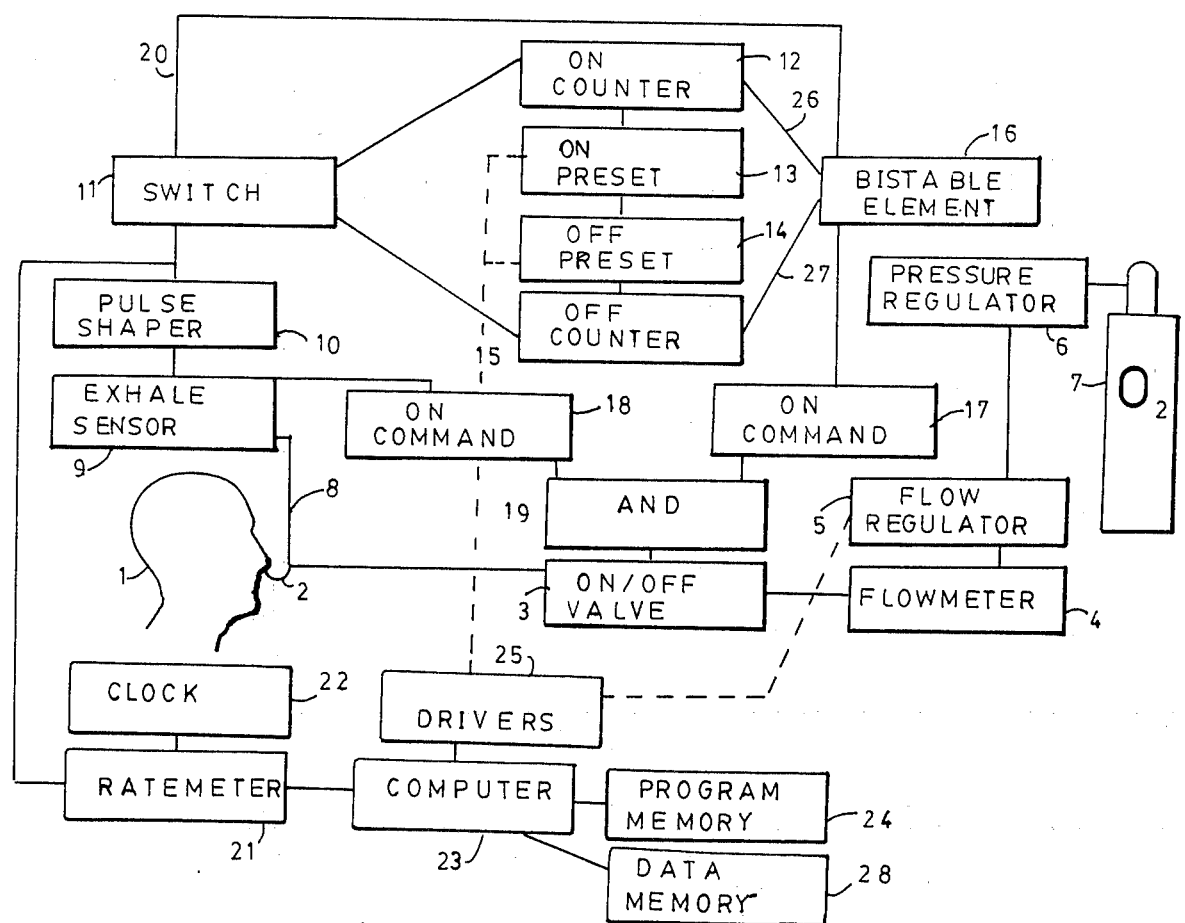
FIG. 2 is a schematic view of another embodiment of the invention including a more versatile responsiveness to increased respiratory rate.

The embodiment of FIG. 2 is similar to the first described embodiment with the addition of elements providing a more adaptive response to increased activity to better provide the increased oxygen thereby required. During the preliminary blood gas measurement process, in addition to determining respiratory rate, gas flow rate and ON/OFF cycle numbers at rest, the same information is acquired at increasing levels of physical activity. These data are stored in data memory 28. Ratemeter 21 receives time information from clock 22 and a pulse from pulse shaper 10 for each respiratory cycle. Ratemeter 21 converts these data into respiratory rate information which is transmitted to microcomputer 23. Microcomputer 23 under guidance of programs stored in program memory 24 finds in data memory 28 the particular settings for ON cycle number and OFF cycle number and gas flow rate corresponding to that particular respiratory rate. This may optionally include interpolation processes. Output drivers 25 use this information output from microcomputer 23 to put a new ON cycle number and OFF cycle number in preset elements 13 and 14 respectively and to readjust flow regulator 5 to provide the optimum gas flow rate.

Many of the individual functional elements illustrated may be incorporated into a microcomputer. Alternatively, a single common counter may be used with alternative ON preset and OFF preset function. Any of a variety of mechanical, pneumatic, fluidic or electronic sensor elements well known in the prior art may be employed to sense one or more phases of the respiratory cycle including a sensing belt around thorax or abdomen. The individual functional elements illustrated may be embodied in fluidic, mechanical or electrical form or in combinations thereof well known in the prior art without departing from the scope of the invention.

The above disclosed invention has a number of particular features which should preferably be employed in combination, although each is useful separately without departure from the scope of the invention. Inasmuch as the invention is subject to many variations, modifications, and changes in detail, it is intended that all matter described above be interpreted as illustrative and not in a limiting sense.

We claim:

1. In apparatus for intermittently supplying respiratory gas to a spontaneously breathing subject which is supplemental to said subject's normal ambient air intake including a gas supply connection means adapted for connection to a gas supply and a subject connection means adapted for delivering said gas to said subject without substantially obstructing said subject's access to ambient air, the improvements comprising: gas conduit means adapted for connection between said gas supply connection means and said subject connection means to provide a fluid path for said gas; valve means interposed in said gas conduit means for controlling an intermittent flow of said gas by sequentially and repetitively opening said valve means for a predetermined number of ON respiratory cycles and closing said valve means for a predetermined number of OFF respiratory cycles; respiratory cycle sensing means adapted for connection to said subject for sensing the respiratory cycles of said subject; counter means connected to said sensing means for summing the number of respiratory cycles; counter presetting means connected to said counter means, causing said counter means to respond when a preset number of cycles has been registered on said counter means, said presetting means including means for storing at least one ON number representing a predetermined number of ON respiratory cycles and at least one OFF number representing a predetermined number of OFF respiratory cycles; valve controller means connected between said counter means and said valve means, wherein said valve controller means is responsive to the response of said counter means upon registration of said preset numbers by operating said valve means, wherein said valve controller means turns said valve means on when a preset OFF number has been registered by said counter means and turns said valve means off when a preset ON number has been registered by said counter means to conserve said gas supply by providing a flow of supplemental gas only during those respiratory cycles when it can be most useful and conserving said gas during other respiratory cycles when it will be less useful.

2. Apparatus of claim 1 wherein: said respiratory cycle sensing means includes means differentially responsive to the inhale phase and the exhale phase of each of said respiratory cycles: said valve controller means including connection to said respiratory cycle sensing means, whereby said valve controller means is further responsive to said respiratory cycle sensing means by turning said valve means off during said exhale phase of each of said respiratory cycles and turning said valve means on during said inhale phase of each of said respiratory cycles only while said counter means is counting up to a preset ON number.

3. The invention of claim 2 wherein at least one of the functional elements is electrically operated.

4. The invention of claim 2 wherein at least one of the functional elements is fluidically operated.

5. The apparatus of claim 2 further comprising: respiratory rate determining means connected to said respiratory cycle sensing means for determining the respiratory rate of said subject; data storage means storing a plurality of predetermined data including ON cycle number data and OFF cycle number data corresponding to a plurality of respiratory rates: data processing means connected to said respiratory rate determining means and said data storage means and said counter presetting means: said data processing means receiving respiratory rate information from said respiratory rate determining means, using said respiratory rate information to select from said data storage means a corresponding ON cycle number means and OFF cycle number means and applying said ON cycle number means and said OFF cycle number means to said counter presetting means to thereby change the ON/OFF gas flow control program to adaptively respond to the changing oxygen requirements of said subject with changing respiratory rate.

6. The apparatus of claim 5 further comprising: gas flow rate adjusting means connected between said gas supply connection means and said subject for controlling the rate of gas flow to said subject when said valve means is on; said data storage means further storing gas flow rate data corresponding to a plurality of respiratory rates; said data processing means further connected to said gas flow rate adjusting means, said data processing means further using said respiratory rate information to select from said data storage means a gas flow rate datum corresponding to said respiratory rate information and said data processing means applying to said gas flow rate adjusting means said gas flow rate datum to thereby change the gas flow rate to adaptively respond to the changing oxygen requirements of said subject with changing respiratory rate.

7. The apparatus of claim 6 wherein at least two of the data processing, presetting, counting or control means are embodied in a computer incorporated into said apparatus.

8. Apparatus of claim 6 wherein said data processing means includes interpolation means, said interpolation means interpolating between stored values in said data storage means to derive data more closely corresponding to a particular respiratory rate.

9. The invention of claim 1 wherein at least one of the functional elements is electrically operated.

10. The invention of claim 1 wherein at least one of the functional elements is fluidically operated.

11. In apparatus for conservatively dispensing respiratory gas to a spontaneously breathing subject which is supplemental to said subject's normal ambient air intake and only during those times when said gas is useful, including a gas connection means adapted for connection to a gas supply and a subject connection means adapted for delivering said gas to said subject without substantially obstructing said subject's access to ambient air, the improvements comprising: gas conduit means connected between said gas connection means and said subject connection means to provide a fluid path for said gas; valve means interposed in said gas conduit means for controlling an intermittent flow of said gas by sequentially and repetitively opening said valve means for a predetermined number of ON respiratory cycles and closing said valve means for a predetermined number of OFF respiratory cycles respiratory cycle sensing means adapted for connection to said subject, said respiratory cycle sensing means being differentially responsive to the inhalation and exhalation phases of the respiratory cycle of said subject for summing the number of respiratory cycles; data storage means storing at least one ON number representing a predetermined number of ON respiratory cycles and at least one OFF number representing a predetermined number of OFF respiratory cycles; control means connected to and receiving data from said (1) data storage means and also connected to and receiving respiratory cycle information from said (2) respiratory cycle sensing means, and also connected to said valve means, whereby said control means, acting on respiratory cycle information from said respiratory cycle sensing means and on data from said data storage means causes said valve means, repetitively and sequentially, to first open only during the inhalation phase of each of a series of respiratory cycles for a predetermined number of ON cycles and then second to remain closed throughout all phases of each of a series of respiratory cycles for a predetermined number of OFF cycles to conserve said gas by only permitting it to flow during periods when it is most useful to said subject.

12. Apparatus of claim 11 further comprising: respiratory rate determining means connected to said respiratory cycle sensing means and said control means for determining respiratory rate information; said data storage means further including predetermined useful number of ON cycles data and predetermined useful number of OFF cycles data corresponding to a plurality of respiratory rates; said control means, further acting on said respiratory rate information received from said respiratory rate determining means as well as on respiratory cycle information causes said valve means to open and close on the basis of ON and OFF cycles number data corresponding to said respiratory rate information received.

13. The apparatus of claim 12, further comprising gas flow rate controller means interposed in said gas connection means to control the rate of gas flow when said valve means is open; said data storage means further including predetermined useful gas flow rate data corresponding to a plurality of respiratory rates; said control means further connected to said gas flow rate controller means, wherein said control means further acting on said respiratory rate information received as well as said useful gas flow rate data causes said gas flow rate controller means to be adjusted to the useful gas flow rate corresponding to said respiratory rate information received.

14. The invention of claim 13, wherein a plurality of the operative functions are embodied in a computer.

15. Apparatus of claim 13, wherein said control means includes interpolation means, said interpolation means interpolating between stored values in said data storage means to derive ON and OFF cycles number data more closely corresponding to the respiratory rate of said subject.

16. Apparatus of claim 12, wherein said control means includes interpolation means, said interpolation means interpolating between stored values in said data storage means to derive ON and OFF cycles number data more closely corresponding to the respiratory rate of said subject.

17. A gas conserving method of intermittently supplying dosages of supplemental respiratory gas to a spontaneously breathing in-vivo respiratory system, said respiratory system having repetitive spontaneous respiratory cycles including an inspiratory period during which ambient air is inhaled followed by an expiratory period during which respired air is exhaled, said method comprising the steps of:
  (1) sensing each respiratory cycle;
  (2) supplying said supplemental respiratory gas along with said ambient air to said respiratory system for a predetermined number of spontaneous respiratory cycles when said gas is most useful;
  (3) discontinuing said supplemental respiratory gas supply to said respiratory system for a predetermined number of subsequent spontaneous respiratory cycles when said gas is less useful;
  (4) automatically and repetitively repeating the steps (1) through (3) for a plurality of successive respiratory cycles to make more effective use of said supplemental gas.

18. In the method of claim 17 step (1) further including differentially sensing said inspiratory period and said expiratory period of said respiratory cycle and step (2) further including supplying said supplemental respiratory gas only during said inspiratory period portion of each respiratory cycle for said predetermined number of spontaneous respiratory cycles when said gas is most useful.

19. The method of claim 18, further including the steps of:
  (5) computing the spontaneous respiratory rate of said respiratory system
  (6) adjusting said predetermined number of spontaneous respiratory cycles in which said supplemental respiratory gas is supplied on the basis of the computed respiratory rate;
  (7) adjusting the predetermined number of said subsequent spontaneous respiratory cycles in which said supplemental respiratory gas is discontinued on the basis of the computed respiratory rate.

20. The method of claim 19, further including the steps of adjusting the flow rate of said supplemental respiratory gas on the basis of said computed respiratory rate.

* * * * *